United States Patent [19]

Copp et al.

[11] Patent Number: 4,950,753

[45] Date of Patent: Aug. 21, 1990

[54] PROCESS FOR 3-EXOMETHYLENECEPHAM SULFOXIDE ESTERS

[75] Inventors: James D. Copp, Rockville; Gregg A. Tharp, Terre Haute, both of Ind.

[73] Assignee: Eli Lilly and Company, Indianapolis, Ind.

[21] Appl. No.: 353,128

[22] Filed: May 17, 1989

[51] Int. Cl.$^5$ .............................................. C07D 501/02
[52] U.S. Cl. ................................. 540/230; 540/215; 540/222
[58] Field of Search ..................... 540/222, 230, 215

[56] References Cited
U.S. PATENT DOCUMENTS 4,052,387 10/1977 Kukoya et al. .................... 540/215

4,190,724 2/1980 Chou .................................. 540/215

Primary Examiner—Nicholas S. Rizzo
Attorney, Agent, or Firm—William C. Martens; Leroy Whitaker; William B. Scanlon

[57] ABSTRACT

3-Exomethylenecepham sulfoxide esters are obtained in improved yields via cyclization of 3-methyl-2-(4-chlorosulfinyl-2-oxo-3-acylamino-1-azetidinyl)-3-butenoic acid esters under anhydrous conditions with stannic chloride in the presence of both an oxo compound, e.g., an ether such as diethyl ether, a ketone such as acetone or methylethyl ketone, and an unsaturated compound, e.g., an alkene such as 1- or 2-hexene, a non-conjugated alkadiene such as 1,4-hexadiene, a cycloalkene such as cyclohexene, an allene, or a non-conjugated cycloalkadiene such as 1,4-cyclohexadiene.

20 Claims, No Drawings

PROCESS FOR 3-EXOMETHYLENECEPHAM SULFOXIDE ESTERS

BACKGROUND OF THE INVENTION

This invention relates to a process for the manufacture of intermediates for β-lactam antibiotics. In particular, it relates to an improved process for the manufacture of 7-substituted amino-3-exomethylenecepham ester sulfoxides.

The preparation of 3-exomethylenecepham sulfoxide esters is carried out by the known two-step process which comprises the conversion of a penicillin sulfoxide ester to a chlorosulfinylazetidinone followed by the cyclization of the latter to a 3-exomethylenecepham sulfoxide ester. The penicillin sulfoxide ester is converted to the intermediate chlorosulfinylazetidinone with an N-chloro halogenating agent as described by Kukolja in U.S. Pat. No. 4,165,315. The 4-chlorosulfinylazetidinone intermediates are described and claimed by Kukolja in U.S. Pat. No. 4,081,440. Chou, U.S. Pat. No. 4,075,203, describes the preparation of 3-exomethylenecepham sulfoxide ester via conversion of the penicillin sulfoxide ester in step 1 to the 4-chlorosulfinylazetidinone with an N-chloro halogenating agent in the presence of an alkylene oxide and calcium oxide. Later, Chou, U.S. Pat. No. 4,289,695, describes an improved process for 3-exomethylenecepham sulfoxide esters by employing an acid scavenging cross-linked polyvinylpyridine polymer in step 1.

Kukolja, U.S. Pat. No. 4,052,387, describes the cyclization of 4-chlorosulfinylazetidinones with a Lewis acid-type Friedel-Crafts catalyst, a Bronsted proton acid-type Friedel-Crafts catalyst or with a metathetic cation-forming agent. Subsequently, Chou, U.S. Pat. No. 4,190,724, describes and claims an improved process which comprises carrying out the Kukolja Friedel-Crafts catalyzed cyclization of a 4-chlorosulfinylazetidinone in the presence of oxo compounds such as ethers, ketones or phosphine oxides. The present invention provides a further improvement of the Kukolja process which comprises carrying out the Friedel-Crafts cyclization in the presence of both an oxo compound of Chou and an unsaturated compound as defined hereinafter.

SUMMARY OF THE INVENTION

According to the process of this invention, a chlorosulfinylazetidinone is reacted in an inert solvent with a Friedel-Crafts catalyst of the type which forms a complex with the chlorosulfinylazetidinone, preferably stannic chloride, in the presence of an oxo compound, e.g., an ether, ketone or phosphine oxide, and in the presence of an alkene, cycloalkene, diene, allene or cyclodiene. The 3-exomethylenecepham sulfoxide ester product is obtained in improved yields generally in the range of between about 2% and about 5% of isolated product.

DETAILED DESCRIPTION

The process of this invention provides a 3-exomethylenecepham sulfoxide ester represented by the formula 1

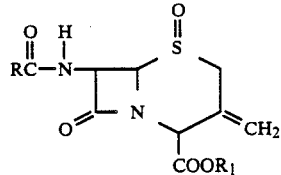

wherein R is the residue of a carboxylic acid RCOOH and $R_1$ is a carboxy-protecting group, by cyclizing a 4-chlorosulfinylazetidin-2-one represented by the formula 2

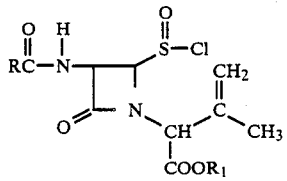

with stannic chloride in the presence of an oxo compound and an unsaturated compound selected from an olefin, cycloolefin, a non-conjugated diene or cyclodiene or an allene. The process is carried out by adding between about 1.5 moles and about 3 moles of stannic chloride per mole of (2) to an anhydrous solution of the 4-chlorosulfinylazetidinone (2) in the presence of between about 1 mole and about 2 moles per mole of (2) of an oxo compound and the unsaturated compound.

The process is carried out at a temperature between about $-15°$ C. and about $45°$ C. in an inert organic solvent. Solvents which may be used are described by Kukolja in U.S. Pat. No. 4,052,387, which is incorporated herein by reference and wherein the basic cyclization process is described. Preferred solvents are aprotic and include the aromatic hydrocarbons such as benzene, toluene, xylene, chlorobenzene and the like, and the halogenated hydrocarbons such as chloroform, methylene chloride, carbon tetrachloride, 1,2-dichloroethane, 1,1,2-trichloroethane, and the like. Preferred solvents are benzene and toluene.

As noted above, the process is carried out under anhydrous conditions. Trace amounts of water are tolerable; however, it is desirable to maintain the reaction mixture in the process as dry as possible.

The unsaturated compound employed in the process is present in an amount corresponding to between about one mole to about two moles per mole of sulfinyl chloride (2). A preferred amount is between about one mole and about 1.5 mole of unsaturated compound per mole of sulfinyl chloride (2). Best results are achieved with 1 mole of unsaturated compound per mole of (2).

The unsaturated compound which can be used in the process is selected from among $C_2$–$C_{10}$ olefins, $C_5$–$C_{10}$ cycloolefins, non-conjugated $C_5$–$C_{10}$ diolefins, $C_3$–$C_{10}$ allenes, and non-conjugated $C_6$–$C_{10}$ cyclodiolefins. Examples of such alkenes, alkadienes, cycloalkenes, allenes and cyclodienes include, for example, the alkenes, ethylene, propylene, 1-butene, 2-butene, 1-pentene, 2-pentene, 1-hexene, 3-hexene, 1-heptene, 3-heptene, 1-octene, 2-nonene, 3-nonene, 1-decene, 5-decene, and like terminal and non-terminal alkenes; non-conjugated alkadienes such as 1,4-pentadiene, 1,4-hexadiene, 3-methyl-1,4-hexadiene, 1,5-hexadiene, 1,5-heptadiene, 1,6-heptadiene, and like dienes; nonconjugated cyclodienes such as 1,4-cyclohexadiene, 1,4-cycloheptadiene, and the like; allenes such as allene, methylallene (1,2-butadiene), dimethylallene (2,3-pentadiene), and the like; cycloalkenes such as cyclopentene, 1-methylcyclopent-2-ene, cyclohexene, cycloheptene, cyclooctene, and the like. The alkene, alkadiene or allene may be straight chained or branched and may be substituted with an inert group, preferably on a saturated carbon atom of the alkene. For example, the unsaturated compound may be substituted with alkyl such as methyl, ethyl or isopropyl; halogen (preferably in a non-allylic position); an esterified carboxy group; an aromatic group such as phenyl or tolyl; nitro; cyano; and alkoxy such as methoxy or ethoxy; and like aprotic substituents which are inert under the conditions of the process.

Non-terminal alkenes may be used in either the cis or trans forms.

Preferred unsaturated compounds of the invention are the alkenes, e.g., 1-pentene, 2-pentene, 1-hexene, 2-hexene, 1-heptene, 1-octene and 1-decene; and the cycloalkenes, cyclopentene and cyclohexene.

In carrying out the process of this invention, the mode of addition of the unsaturated compound may vary. For example, the unsaturated compound may be added to the solution of the sulfinyl chloride (2) in the inert solvent and a mixture of the stannic chloride and oxo compound added thereafter. Alternatively, the unsaturated compound is mixed with the stannic chloride and the oxo compound in an inert dry solvent and the mixture added to the solution of (2).

The oxo compounds used in the process are described by Chou, U.S. Pat. No. 4,190,724, which is incorporated herein by reference, and are selected from among the group

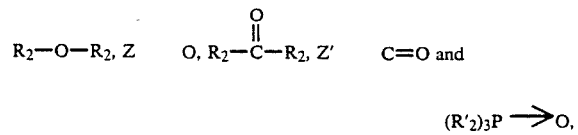

wherein each $R_2$ is independently $C_1$–$C_4$ alkyl; each $R'_2$ is independently $C_1$–$C_4$ alkyl, $C_5$–$C_6$ cycloalkyl, phenyl or phenyl substituted by $C_1$–$C_4$ alkyl, $C_1$–$C_4$ alkoxy, or halogen; Z is —$CH_2$—$_m$, —$CH_2$—$CH_2$—O—$CH_2$—$CH_2$—, or —$CH_2$—O—$CH_2CH_2CH_2$—; m is 4 or 5; and Z' is

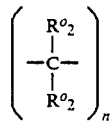

wherein each of $R°_2$ is hydrogen or $C_1$–$C_4$ alkyl, and n is 3 to 6. Preferred oxo compounds are diethyl ether, di-n-propyl ether, acetone and methylethyl ketone.

The process of this invention is carried out as follows. The 4-chlorosulfinylazetidinone (2) is dissolved in an anhydrous inert organic solvent, the solution cooled to a temperature of about 10° C. to about 15° C., and between about 1 mole and about 2 moles per mole of (2) of the unsaturated compound is added. The solution is stirred for about 1 to 5 minutes and a cold (0° to 5° C.) slurry of stannic chloride and the oxo compound in an inert solvent is added rapidly. The resulting complex which forms is stirred at about room temperature for about 6 h to about 12 h. The complex is separated from the reaction mixture, e.g., by filtration or centrifugation, is washed with an inert solvent and decomposed with a lower alcohol such as methyl alcohol. The 3-exomethylenecepham sulfoxide ester forms as a solid precipitate, is filtered, washed and dried for subsequent use.

The 4-chlorosulfinylazetidinones (2) used in the process are known compounds and are described by Kukolja in U.S. Pat. No. 4,081,440 incorporated herein by reference. Examples of the starting materials which are used in the process are t-butyl 3-methyl-2-(4-chlorosulfinyl-2-oxo-3-phenylacetylamino-1-azetidinyl)-3-butenoate, t-butyl 3-methyl-2-(4-chlorosulfinyl-2-oxo-3-phenoxyacetylamino-1-azetidinyl)-3-butenoate, diphenylmethyl 3-methyl-2-(4-chlorosulfinyl-2-oxo-3-phenoxyacetylamino-1-azetidinyl)-3-butenoate, p-methoxybenzyl 3-methyl-2-(4-chlorosulfinyl-2-oxo-3-phenylacetylamino-1-azetidinyl)-3-butenoate, p-nitrobenzyl 3-methyl-2-(4-chlorosulfinyl-2-oxo-3-phenoxy-acetylamino-1-azetidinyl)-3-butenoate, diphenylmethyl 3-methyl-2-(4-chlorosulfinyl-2-oxo-3-benzoylamino-1-azetidinyl)-3-butenoate, p-nitrobenzyl 3-methyl-2-[4-chlorosulfinyl-2-oxo-3-(α-t-butyloxycarbonylamino-phenylacetylamino)-1-azetidinyl]-3-butenoate, benzyl 3-methyl-2-(4-chlorosulfinyl-2-oxo-3-phenoxyacetylamino-1-azetidinyl)-3-butenoate, and benzhydryl 3-methyl-2-(4-chlorosulfinyl-2-oxo-3-acetylamino-1-azetidinyl)-3-butenoate. Preferred azetidinones (2) are represented by the formula 2 when R is benzyl, phenoxymethyl or thienylmethyl. A preferred ester group $R_1$ of formula 2 is benzyl or substituted benzyl, especially p-nitrobenzyl.

As was mentioned hereinabove, the use of the above-defined unsaturated compounds in the known cyclization process results in improved yields of 3-exomethylenecepham sulfoxide ester. Yields of sulfoxide ester generally obtained are for 2% to 5% greater than control preparations. Such increased yields are of substantial economic value in the manufacture of large quantities of the 3-exomethylenecepham sulfoxide ester. The 3-exomethylenecepham sulfoxide ester (1) is used as an intermediate in the preparation of cephalosporin antibiotics, for example, cefaclor, 7β-phenylglycylamino-3-chloro-3-cephem-4-carboxylic acid by known methods. The intermediate (1) also may be used to prepare cephalexin, 7β-phenylglycylamino-3-methyl-3-cephem-4-carboxylic acid. Accordingly, the increased yields realized in the process of this invention result in increased production of these valuable antibiotic compounds.

The manner in which the unsaturated compounds function to provide increased yields of (1) has as yet not been determined. The possibility exists that the olefins, dienes and allenes function as ligands to provide further stabilization of the tin complex formed with the sulfinyl chloride (2) and stannic chloride over that provided by the Chou, supra, oxo compound. However, whether the unsaturated compounds function as ligands or in some other manner is uncertain at present.

The following Examples are provided to further describe the invention and are not to be construed as limitations thereof.

EXAMPLE 1

A solution of 0.096 mole of p-nitrobenzyl 3-methyl-2-(4-chlorosulfinyl-2-oxo-3-phenoxyacetylamino-1-azetidinyl)-3-butenoate in 800 ml of dry toluene is cooled to 10° C. and 0.096 mole of 1-hexene is added. The solution is stirred for about one minute and a cold (0° to 5° C.) slurry of stannic chloride-diethyl ether in toluene is added rapidly.

The stannic chloride-diethyl ether slurry is prepared as follows. Toluene (25 ml) is cooled to 0° C. and 9.2 ml (0.089 mole) of anhydrous diethyl ether is added. Stannic chloride (19.0 ml, 0.164 mole) is added while the temperature is maintained below 20° C. The resulting slurry is cooled to 0° C.-5° C. before being added to the sulfinyl chloride-hexene reaction mixture.

Following the addition of the stannic chloride-ether mixture, the insoluble complex which is formed is stirred at 25° C. to 30° C. for from 6 h to about 12 h.

The orange complex is filtered and washed with 80 ml of toluene. The filter cake is treated with 250 ml of methanol to decompose the complex and provide a light-yellow slurry which is stirred at 25° C.-30° C. for 15 min and then at 0° C.-5° C. for about 3 h and 45 min. The product, p-nitrobenzyl 7$\beta$-phenoxyacetylamino-3-exomethylenecepham-4-carboxylate, 1-oxide, is filtered, washed with 100 ml of methanol and dried in a vacuum oven at 50° C. overnight. A typical preparation carried out as described above provides about 36 g (73% assay corrected) of the product as an off-white solid.

The following Examples were carried out by substituting the indicated unsaturated compound for the 1-hexene employed in Example 1.

| Ex. No. | Unsaturated Cpd. | No. of Runs | Average % Yield Increase Over Control |
|---|---|---|---|
| 2 | 1-heptene | 7 | 2.8 |
| 3 | 1-pentene | 8 | 3.0 |
| 4 | 1-decene | 6 | 4.8 |
| 5 | 1-octene | 6 | 4.6 |
| 6 | 2-hexene | 8 | 3.6 |
| 7 | 2-pentene | 8 | 2.4 |
| 8 | 1,5-hexadiene | 4 | 3.2 |
| 9 | cyclohexene | 7 | 3.6 |
| 10 | cyclopentene | 7 | 3.3 |

EXAMPLE 11

Diphenylmethyl 7$\beta$-phenylacetylamino-3-exomethylenecepham-4-carboxylate

Diphenylmethyl 3-methyl-2-(4-chlorosulfinyl-2-oxo-3-phenylacetylamino-1-azetidinyl)-3-butenoate is cyclized under the conditions of Example 1 in the presence of 1-decene to provide the title compound.

We claim:

1. In the presence for preparing a 3-exomethylenecepham sulfoxide ester of the formula

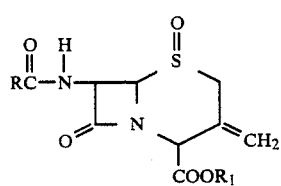

wherein R is the residue of a carboxylic acid and $R_1$ is a carboxylic acid protecting group, which comprises adding to a solution of a 4-chlorosulfinylazetidin-2-one of the formula

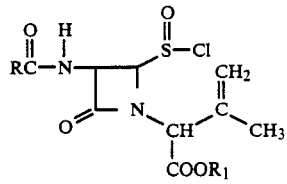

in an inert solvent under substantially anhydrous conditions at a temperature between about $-15°$ C. and about 45° C., between about 1.5 and about 3 moles of stannic chloride per mole of said azetidinone in the presence of between about 1 and about 2.0 moles per mole of said azetidinone of an oxo compound; separating the complex formed; and decomposing said complex; the improvement which comprises carrying out the addition of stannic chloride and said oxo compound in the presence of an unsaturated compound selected from the group of a $C_2$-$C_{10}$ olefin, a $C_5$-$C_{10}$ cyclic olefin, a $C_5$-$C_{10}$ nonconjugated diolefin, a $C_3$-$C_{10}$ allene, and a $C_6$-$C_{10}$ nonconjugated cyclic diene.

2. The process of claim 1 wherein the unsaturated compound is a non-conjugated $C_5$-$C_{10}$ alkadiene.

3. The process of claim 1 wherein the unsaturated compound is a $C_3$-$C_{10}$ allene.

4. The process of claim 1 wherein the unsaturated compound is a $C_5$-$C_{10}$ cycloalkene.

5. The process of claim 4 wherein the cycloalkene is cyclopentene or cyclohexene.

6. The process of claim 1 wherein the unsaturated compound is a $C_2$-$C_{10}$ alkene.

7. The process of claim 6 wherein the alkene is a $C_5$-$C_8$ alkene.

8. The process of claim 7 wherein the alkene is a straight chain or branched chain alkene.

9. The process of claim 8 wherein the alkene is 1-pentene, 1-hexene, 2-hexene, 1-heptene or 1-octene.

10. The process of claim 1 wherein the oxo compound is of the formulae

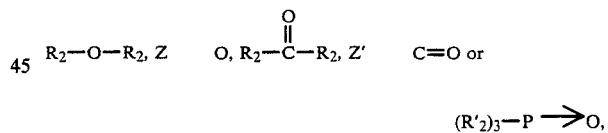

wherein each $R_2$ is independently $C_1$-$C_4$ alkyl; each $R'_2$ is independently $C_1$-$C_4$ alkyl, $C_5$-$C_6$ cycloalkyl, phenyl or phenyl substituted by $C_1$-$C_4$ alkyl, $C_1$-$C_4$ alkoxy or halogen; Z is $-CH_2-_m$, $-CH_2-O-CH_2CH_2-$, or $-CH_2-O-CH_2-_3$; m is 4 or 5; and Z' is

wherein each $R°_2$ is hydrogen or $C_1$-$C_4$ alkyl, and n is 3 to 6.

11. The process of claim 10 wherein R is benzyl, phenoxymethyl or 2-thienyl and $R_1$ is benzyl or substituted benzyl.

12. The process of claim 10 wherein R is phenoxymethyl and $R_1$ is p-nitrobenzyl.

13. The process of claim 12 wherein the oxo compound is of the formula $R_2-O-R_2$ or

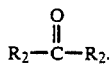

14. The process of claim 13 wherein the oxo compound is diethyl ether or acetone.

15. The process of claim 1 wherein a mixture of the stannic chloride and oxo compound are added to a solution of the 4-chlorosulfinylazetidinone containing the unsaturated compound.

16. The process of claim 1 wherein a mixture of stannic chloride with the oxo compound and the unsaturated compound is added to a solution of the 4-chlorosulfinylazetidinone.

17. The process of claim 1 wherein the unsaturated compound is present in an amount corresponding to between about 1 mole to about 2 moles of unsaturated compound per mole of 4-chlorosulfinylazetidinone.

18. The process of claim 1 wherein R is phenoxymethyl, $R_1$ is 4-nitrobenzyl, the oxo compound is diethyl ether, and the unsaturated compound is a $C_5-C_8$ alkene.

19. The process of claim 18 wherein the alkene is a straight chain 1-alkene.

20. The process of claim 19 wherein a mixture of the stannic chloride and oxo compound is added to the solution of the 4-chlorosulfinylazetidinone containing the 1-alkene.

* * * * *

UNITED STATES PATENT AND TRADEMARK OFFICE
CERTIFICATE OF CORRECTION

PATENT NO. : 4,950,753
DATED : August 21, 1990
INVENTOR(S) : James D. Copp et al.

It is certified that error appears in the above-identified patent and that said Letters Patent is hereby corrected as shown below:

Column 5, Claim 1, first line - "presence" should be --process--.

Column 6, Claim 1, line 22 - "nonconjugated" should be -- non-conjugated --.

Column 6, Claim 1, line 23 - "nonconjugated" should be -- non-conjugated --.

Column 6, Claim 10, line 45 - "$R_2-O-R_2$, Z    O, $R_2-C-R_2$  Z'  C=O" should be --$R_2-O-R_2$, Z    O, $R_2-C-R_2$, Z'    C=O Column 6, Claim 10, line 53 - "$-CH_2-_m$, $-CH_2O-CH_2CH_2-$" should be -- $(CH_2)_m$, $-CH_2CH_2-O-CH_2CH_2-$ --

Column 6, Claim 10, line 54 - "$-CH_2-O-CH_2-_3$" should be -- $-CH_2-O(CH_2)_3$ --.

Signed and Sealed this

Eighteenth Day of August, 1992

Attest:

DOUGLAS B. COMER

Attesting Officer

Acting Commissioner of Patents and Trademarks